United States Patent
Singh et al.

(10) Patent No.: US 11,254,675 B2
(45) Date of Patent: Feb. 22, 2022

(54) PROCESS FOR PREPARATION OF GRAPIPRANT

(71) Applicant: CADILA HEALTHCARE LIMITED, Gujarat (IN)

(72) Inventors: Kumar Kamlesh Singh, Gujarat (IN); Jitendra Maganbhai Gajera, Gujarat (IN); Sumer Singh Chundavat, Gujarat (IN); Dipak Ambalal Patel, Gujarat (IN)

(73) Assignee: CADILA HEALTHCARE LIMITED, Ahmedabad (IN)

( * ) Notice: Subject to any disclaimer, the term of this patent is extended or adjusted under 35 U.S.C. 154(b) by 0 days.

(21) Appl. No.: 16/991,323

(22) Filed: Aug. 12, 2020

(65) Prior Publication Data
US 2021/0079000 A1    Mar. 18, 2021

(30) Foreign Application Priority Data

Aug. 12, 2019  (IN) .............................. 201921032548
Apr. 1, 2020   (IN) .............................. 202021014512

(51) Int. Cl.
  *C07D 471/06*  (2006.01)
  *A61K 31/64*   (2006.01)
  *C07D 213/76*  (2006.01)

(52) U.S. Cl.
  CPC ............ *C07D 471/06* (2013.01); *A61K 31/64* (2013.01); *C07D 213/76* (2013.01)

(58) Field of Classification Search
  CPC .......................... C07D 471/04; C07D 471/06
  See application file for complete search history.

(56) References Cited

U.S. PATENT DOCUMENTS 6,710,054 B2   3/2004   Nakao et al.
7,960,407 B2   6/2011   Haruta et al.
9,265,756 B2   2/2016   Newbold et al.

*Primary Examiner* — Patricia L Morris
(74) *Attorney, Agent, or Firm* — Ladas & Parry LLP

(57) ABSTRACT

The invention relates to process for the preparation of grapiprant and its intermediates thereof. The invention also relates to grapiprant having a purity 98% or more and compounds of Formula (A), (B), (C) and (D) in an amount of 0.5 or less, relative to grapiprant, by area percentage of HPLC. The invention also relates to an amorphous form of grapiprant and process for preparation thereof.

4 Claims, 1 Drawing Sheet

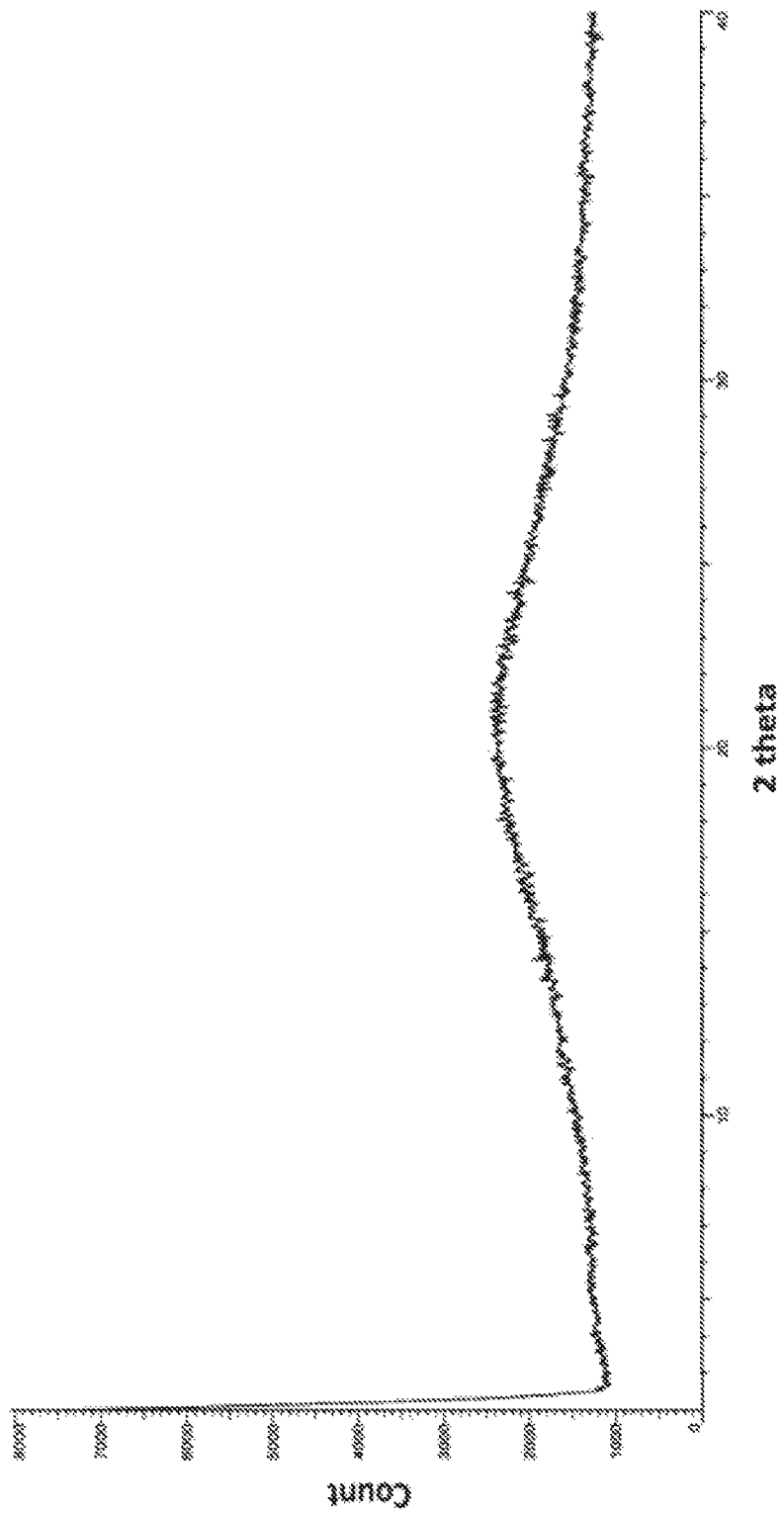

PROCESS FOR PREPARATION OF GRAPIPRANT

FIELD OF THE INVENTION

The invention relates to process for the preparation of grapiprant and its intermediates thereof. The invention also relates to grapiprant having a purity 98% or more and compounds of Formula (A), (B), (C) and (D) in an amount of 0.5 or less, relative to grapiprant, by area percentage of HPLC. The invention also relates to an amorphous form of grapiprant and process for preparation thereof.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Grapiprant is a Non-COX inhibiting NSAID that specifically targets the EP4 receptor. It is indicated for the control of pain and inflammation associated with osteoarthritis in dogs. Its chemical name is 1-[2-(4-{2-ethyl-4,6-dimethyl-imidazo[4,5-c]pyridin-1-yl}phenyl)ethyl]-3-(4-ethylphenyl)sulfonylurea. It has structural formula as represented by compound of Formula (I).

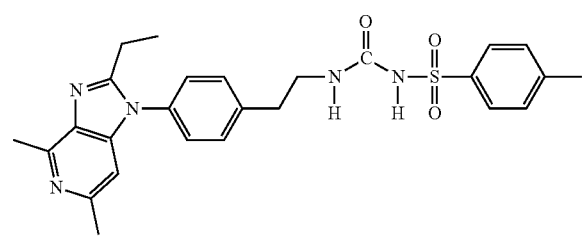

(I)

U.S. Pat. No. 6,710,054 B2 discloses the compound of Formula (I) and various routes of synthesis for the preparation of aryl or heteroaryl fused imidazole compounds as anti-inflammatory and analgesic agents.

U.S. Pat. No. 7,960,407 B2 discloses various crystalline forms of grapiprant which are designated as Form A and Form B.

U.S. Pat. No. 9,265,756 B2 discloses other crystalline form of grapiprant which are designated as Form X, $X_2$, $X_3$, F, K, L, M and N.

The major drawback of the methods described in the prior art is that involves isolation by column chromatography or such techniques which are not a suitable for the scale up and commercial production and feasible only at laboratory scale. Therefore, the object of the present invention is to provide a cost effective and commercially feasible process for the production of grapiprant. The present invention also discloses amorphous form of grapiprant and its amorphous solid dispersion.

SUMMARY OF THE INVENTION

In one general aspect, there is provided grapiprant having a purity 98% or more and compounds of Formula (A), (B), (C), and (D), in an amount of 0.5 or less, relative to grapiprant, by area percentage of HPLC:

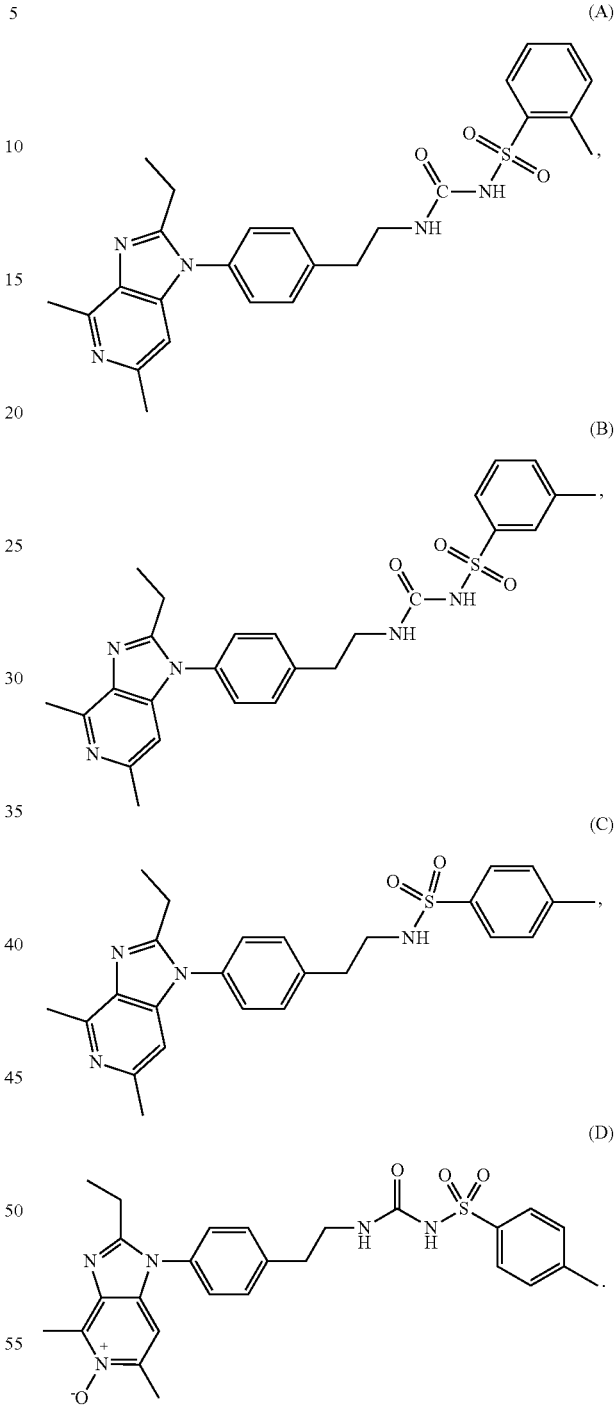

In another general aspect, there is provided grapiprant having a purity 98% or more and the compounds of Formula (A), (B), (C), and (D), in an amount of 0.5 or less, relative to grapiprant, by area percentage of HPLC.

In another general aspect, there is provided an amorphous solid dispersion of grapiprant and a polymer.

In another general aspect, there is provided an amorphous solid dispersion of grapiprant with a polymer having a purity 98% or more and the compounds of Formula (A), (B), (C), and (D), in an amount of 0.5 or less, relative to grapiprant, by area percentage of HPLC.

In another general aspect, there is provided a compound of Formula (A), (B), (C), (D), and (VI):

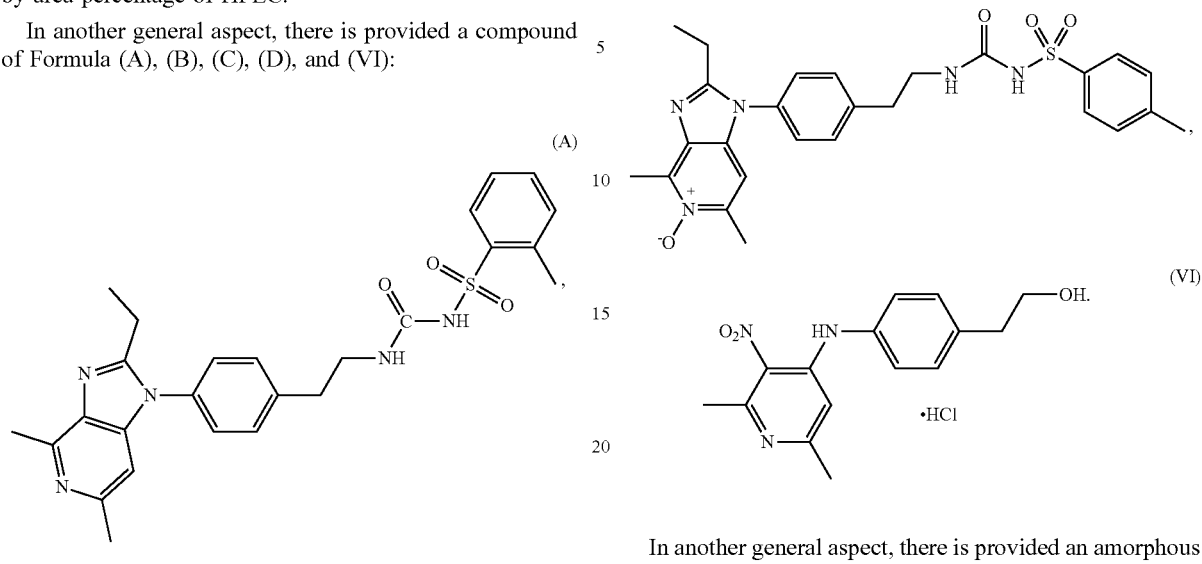

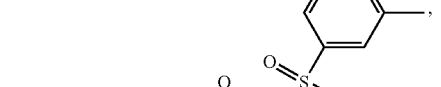

In another general aspect, there is provided an amorphous form of grapiprant.

In another general aspect, there is provided a process for the preparation of amorphous grapiprant, the process comprising:

(a) providing a solution of grapiprant in one or more solvents; and (b) obtaining the amorphous grapiprant by the removal of the solvent.

In another general aspect, there is provided a process for the preparation of an amorphous solid dispersion of grapiprant and a polymer, the process comprising:

(a) dissolving grapiprant in one or more solvent;

(b) adding a polymer; and (c) removing the solvent to obtain the amorphous solid dispersion of grapiprant.

In another general aspect, there is provided a process for the preparation of grapiprant comprising reacting a compound of Formula (II),

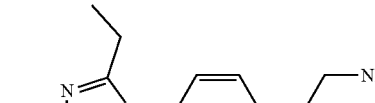

with ethyl(p-tolylsulfonyl)carbamate.

In another general aspect, there is provided a process for the preparation of grapiprant comprising reacting a compound of Formula (II),

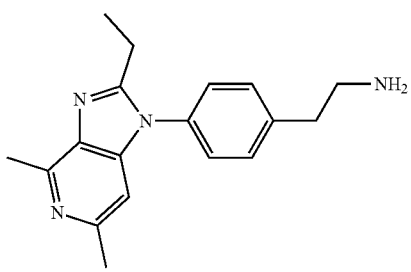

(II)

with ethyl(p-tolylsulfonyl)carbamate in the presence of a base.

In another general aspect, there is provided a process for the preparation of the compound of Formula (II),

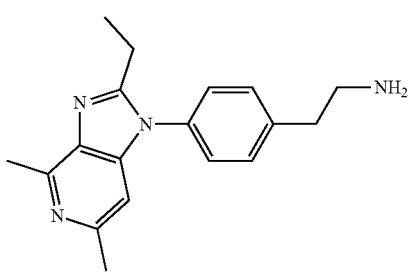

(II)

the process comprising:

(a) reacting a compound of Formula (VII) with a compound of Formula (VIII),

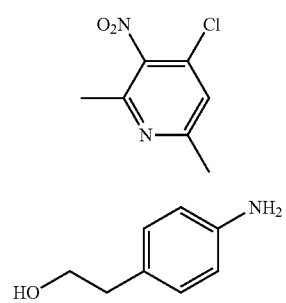

(VII)

(VIII)

to obtain a compound of Formula (VI);

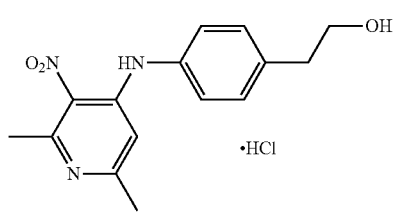

(VI)

(b) converting the compound of Formula (VI) into a compound of Formula (V);

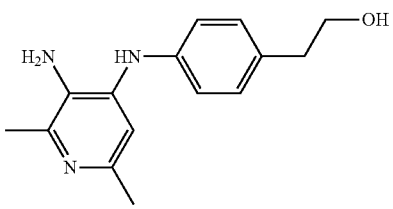

(V)

(c) converting the compound of Formula (V) into a compound of Formula (IV);

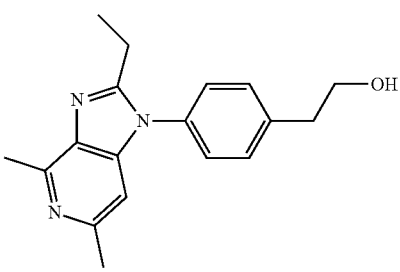

(IV)

(d) converting the compound of Formula (IV) into a compound of Formula (III); and (III)

(e) converting the compound of Formula (III) into a compound of Formula (II).

In another general aspect, there is provided a pharmaceutical composition comprising grapiprant and one or more of compounds of Formula (A), (B), (C), and (D).

In another general aspect, there is provided a pharmaceutical composition comprising grapiprant and one or more of compounds of Formula (A), (B), (C), and (D), wherein the grapiprant is having a purity of about 98% or more, and the compounds of Formula (A), (B), (C), and (D), are present in amount an amount of 0.5 or less, relative to grapiprant, by area percentage of HPLC.

In another general aspect, there is provided a pharmaceutical composition comprising grapiprant and one or more of compounds of Formula (A), (B), (C), and (D), wherein the grapiprant is having a purity of 98% or more, and the compounds of Formula (A), (B), (C), and (D), are present in an amount of 0.2 or less relative to grapiprant, by area percentage of HPLC.

In general, the grapiprant in the composition may be in amorphous form or in any crystalline or hydrated or anhydrous form.

In another general aspect, there is provided grapiprant having a purity of 95% or more, 98% or more, or 99% or more, or 99.5% or more, or 99.8% or more, or 99.9% or more, by area percentage of HPLC.

In another general aspect, there is provided a pharmaceutical composition comprising amorphous solid dispersion of grapiprant and one or more of compounds of Formula (A), (B), (C), and (D), wherein the grapiprant is having a purity of about 98% or more, and one or more of compounds of Formula (A), (B), (C), and (D), in an amount an amount of 0.5% or less, relative to grapiprant, by area percentage of HPLC.

In another general aspect, there is provided grapiprant having particle size distributions wherein the 10th volume percentile particle size (D10) is 50 μm or less, the 50th volume percentile particle size (D50) is 200 μm or less, or the 90th volume percentile particle size (D90) is 400 μm or less, or any combination thereof.

In another general aspect, there is provided a pharmaceutical composition comprising an amorphous form or an amorphous solid dispersion of grapiprant and one or more of compounds of Formula (A), (B), (C), and (D), wherein the grapiprant is having a purity of 98% or more, and the compounds of Formula (A), (B), (C), and (D), in an amount of 0.5% or less, relative to grapiprant, by area percentage of HPLC, and a polymer together with one or more of pharmaceutically acceptable carriers, excipients or diluents.

BRIEF DESCRIPTION OF THE FIGURES AND DRAWINGS

FIG. 1: X-ray diffractogram (XRD) of the amorphous grapiprant of Formula (I).

DETAILED DESCRIPTION OF THE INVENTION

The aforementioned general and further specific aspects of the invention are fulfilled by the description of the invention provided herein after.

The terms 'reacting', 'treating' and 'condensing' are generally interchangeable and used in their ordinary meaning as they are in the field of the invention, unless otherwise specifically described.

The terms 'isolating', 'obtaining' and 'purifying' are generally interchangeable and include but not specifically limited to extraction, evaporation, crystallization, filtration, recrystallization or chromatographic operations.

The term 'converting' relates to reacting the compound, to which it refers, with another compound and/or reagent, and/or subjecting it to condition(s) such that it transforms to another compound as results of such process or treatment.

The product(s) obtained may further be purified to obtain them in purer forms.

The product(s) obtained may further be dried additionally to achieve desired level of moisture and/or residual solvents.

The product(s) obtained may further be converted to any other physical forms thereof which includes but not specifically limited to salt(s), solvate(s), hydrate(s), co-crystal(s) and solid dispersion(s) in either crystalline or amorphous forms.

As used herein, the term "solid dispersion" means any solid composition having at least two components. In certain embodiments, a solid dispersion as disclosed herein includes an active ingredient grapiprant dispersed among at least one other component, for example a polymer.

The product(s) obtained may further be subjected to physical processing which includes, but not limited to, pressing, crushing, triturating, milling or grinding to adjust the particle size of the product(s) to desired levels.

As used herein, "Particle Size Distribution (PSD)" means the cumulative volume size distribution of equivalent spherical diameters as determined by laser diffraction in Malvern Master Sizer 2000 equipment or its equivalent.

As used herein, the term "solution" or "reaction mixture" does not limit to a clear solution only and includes any hazy or opaque mass obtained.

The term "composition" means two or more substances present in combination, not in fixed proportions and not with chemical bonding.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

In one general aspect, there is provided grapiprant having a purity 98% or more, and compounds of Formula (A), (B), (C), and (D) in an amount of 0.5% or less, relative to grapiprant, by area percentage of HPLC,

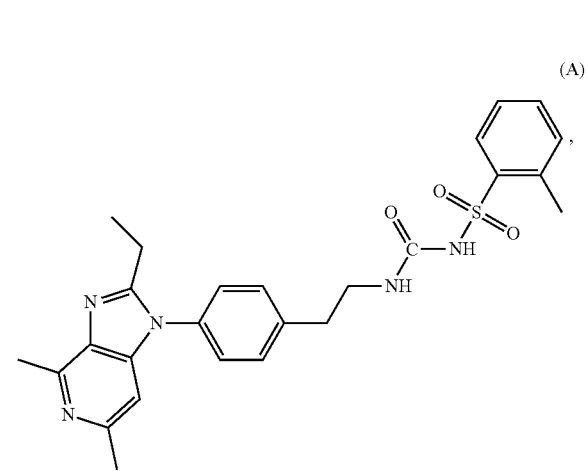

(A)

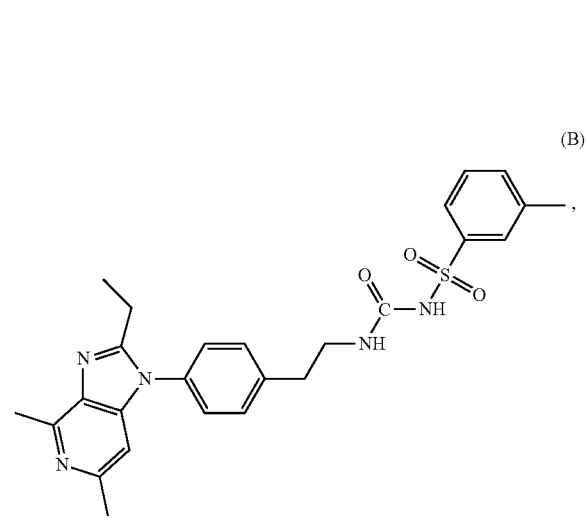

(B)

-continued

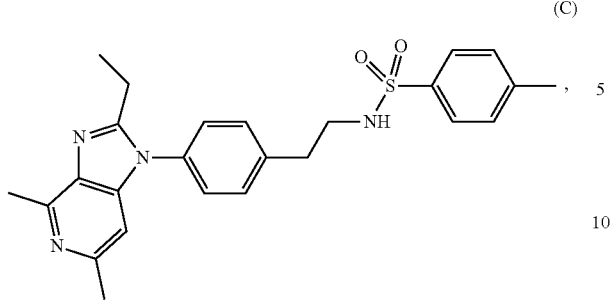
(C)

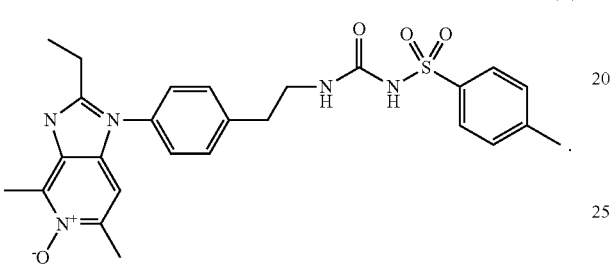
(D)

In another general aspect, there is provided grapiprant having a purity 98% or more, and the compounds of Formula (A), (B), (C), and (D) in an amount of 0.5% or less, relative to grapiprant, by area percentage of HPLC.

In another general aspect, there is provided an amorphous solid dispersion of grapiprant and a polymer.

In another general aspect, there is provided a process for the preparation of an amorphous solid dispersion of grapiprant with a polymer, comprising:

(a) dissolving grapiprant in one or more solvent;

(b) adding a polymer; and (c) removing the solvent to obtain the amorphous solid dispersion of grapiprant.

In general, the solvent at the step (a) is selected from one or more of methanol, ethanol, isopropanol, 1-butanol, tert-butanol, acetonitrile, dichloromethane, acetone, cyclohexane, hexane, dimethyl formamide and dimethyl sulphoxide.

In general, the polymer at the step (b) may be a non-ionic polymer or an ionic polymer. The polymer comprises of hydroxypropylmethyl cellulose acetate succinate (HPMC-AS), hydroxypropylmethyl cellulose (HPMC), methacrylic acid copolymers, polyvinyl pyrrolidone (PVP), and co-povidone.

In general, the removal of the solvents at the step (c) comprises one or more of distillation, distillation under vacuum, spray drying, agitated thin film drying ("ATFD"), and freeze drying (lyophilization).

In another general aspect, there is provided an amorphous solid dispersion of grapiprant and a polymer having a purity 98% or more, and the compounds of Formula (A), (B), (C), and (D) in an amount of 0.5% or less, relative to grapiprant, by area percentage of HPLC.

In another general aspect, there is provided a compound of Formula (A), (B), (C), (D), and (VI),

(A)

(B)

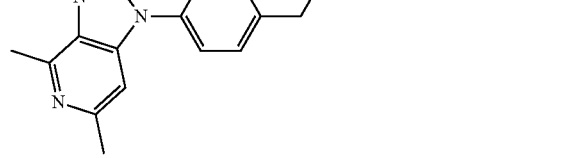
(C)

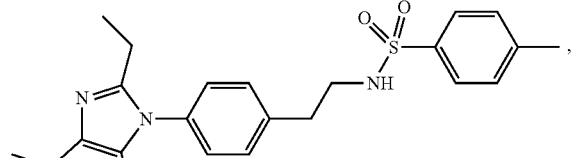
(D)

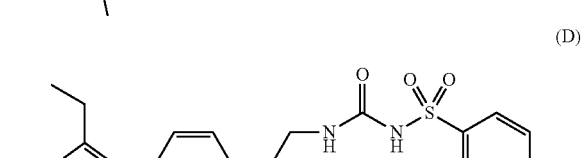
(VI)

In another general aspect, there is provided an amorphous form of grapiprant.

In another general aspect, there is provided a process for the preparation of amorphous grapiprant, the process comprising:
(a) providing a solution of grapiprant in one or more solvents; and
(b) obtaining the amorphous grapiprant by the removal of the solvent.

In general, the solvent at step (a) is selected from one or more of $C_1$-$C_6$ alcohols selected from methanol, ethanol, isopropanol, 1-butanol and tert-butanol; nitriles selected from acetonitrile and propionitrile; halogenated solvents selected from chloroform, ethylene dichloride, carbon tetrachloride, and dichloromethane; ketones selected from acetone; aliphatic hydrocarbons selected from cyclohexane and hexane; aromatic hydrocarbons selected from toluene and xylene; dimethyl sulphoxide; dimethyl formamide, ethers selected from THF and dioxane; and mixtures thereof.

In general, the removal of the solvents at step (b) comprises one or more of distillation, distillation under vacuum, spray drying, agitated thin film drying ("ATFD"), and freeze drying (lyophilization).

In another general aspect, there is provided a process for the preparation of grapiprant comprising reacting a compound of Formula (II),

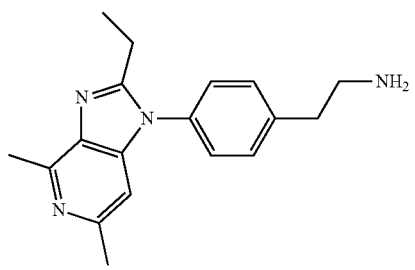

(II)

with ethyl(p-tolylsulfonyl)carbamate.

In another general aspect, there is provided a process for the preparation of grapiprant comprising reacting a compound of Formula (II),

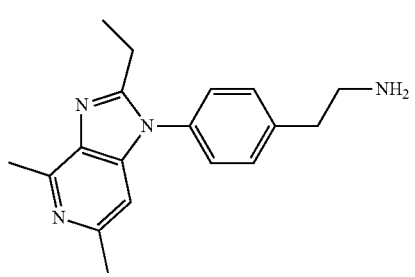

(II)

with ethyl(p-tolylsulfonyl)carbamate in the presence of a base.

In general, the reaction of the compound (II) and ethyl (p-tolylsulfonyl)carbamate may be performed in one or more solvents selected from ethyl acetate, isopropyl acetate, butyl acetate, benzene, toluene, xylene, methylene dichloride, ethylene dichloride, chloroform, and chlorobenzene. In particular, toluene may be used.

In general, the base for the reaction can be selected from sodium hydroxide, potassium hydroxide, lithium hydroxide, sodium carbonate, potassium carbonate lithium carbonate, sodium bicarbonate, potassium bicarbonate, sodium hydride, potassium tert-butoxide or triethyl amine, diisopropyl amine, diisopropylethylamine, pyridine, morpholine, piperidine, DBU or DABCO. In particular, triethyl amine can be used.

In general, the temperature range for the reaction may be selected from 50 to 100° C. Preferably, the reaction is carried out at 80-85° C.

In another general aspect, there is provided a process for preparation of grapiprant, the process comprising:
(a) reacting a compound of Formula (VII) with a compound of Formula (VIII),

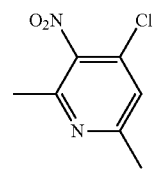

(VII)

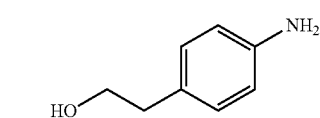

(VIII)

to obtain a compound of Formula (VI);

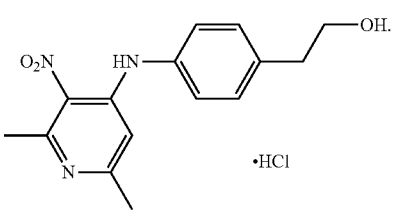

(VI)

(b) converting the compound of Formula (VI) into a compound of Formula (V);

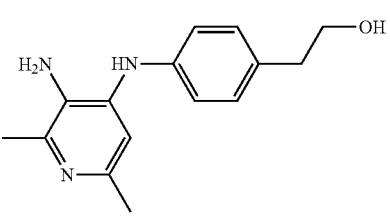

(V)

(c) converting the compound of Formula (V) into a compound of Formula (IV);

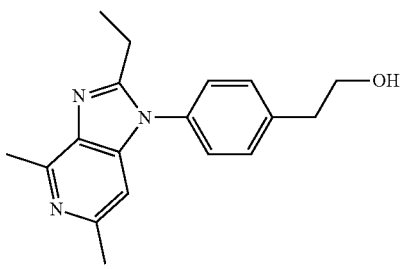

(IV)

(d) converting the compound of Formula (IV) into a compound of Formula (III); and

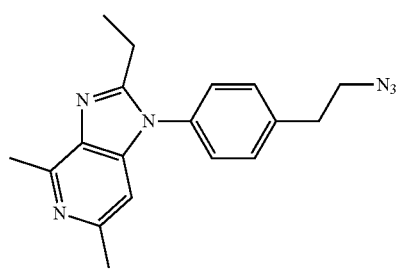

(III)

(e) converting the compound of Formula (III) into a compound of Formula (II).

In general, the reaction of 2-(4-aminophenyl)ethyl alcohol in step (a) of Formula (VIII) can be reacted with 4-chloro-2,6-dimethyl-3-nitropyridine compound of Formula (VII) in the presence of the polar aprotic solvents which may be selected from N-methyl pyrrolidone, dimethyl formamide and dimethyl sulfoxide. Particularly, the reaction can be carried out in the presence of N-methyl-2-pyrrolidone at a temperature in the range of from about 50 to 120° C. Particularly, 75-110° C. to obtain a compound of Formula (VI).

In general, the compound of Formula (VI) at step (b) is treated with reducing reagent in one or more solvents to obtain a compound of Formula (V). The reaction can be performed at temperature range selected from 60-70° C. In particular, at 63-68° C.

In general, the reducing reagents for the reaction can be selected from Palladium/carbon, Raney Ni, ruthenium, rhodium and platinum and hydrazine hydrate, zinc metal in aqueous ammonium chloride, zinc metal with sodium hydroxide or using lithium aluminium hydride. In particular, Raney Ni and hydrazine hydrate can be used.

In general, the solvents for the reaction can be selected from methylene dichloride, ethylene dichloride, chloroform, chlorobenzene, N,N'-dimethyl formamide and dimethyl sulfoxide, $C_1$-$C_6$ alcohols. In particular, methylene dichloride and methanol may be used.

In general, the compound of Formula (V) in step (c) is treated with propionic acid and propionic anhydride at temperature ranging from 80-150° C. Particularly, temperature ranging from 100-130° C.

It is then reacted with a base, which may be selected from one or more of alkali metal carbonates selected from sodium carbonate, potassium carbonate and cesium carbonate; alkali metal bicarbonates selected from sodium bicarbonate and potassium bicarbonate; alkali metal hydroxides selected from sodium hydroxide, potassium hydroxide, magnesium hydroxide and lithium hydroxide; alkali metal hydride such as sodium hydride and potassium hydride. Preferably using NaOH in presence of one or more solvents to obtain a compound of Formula (IV).

Solvent for the reaction can be selected from one or more of water, $C_1$-$C_6$-alcohols selected from methanol, ethanol, isopropanol, 1-butanol and tert-butanol; nitriles selected from acetonitrile and propionitrile; halogenated solvents selected from chloroform, ethylene dichloride, carbon tetrachloride and dichloromethane; ketones selected from acetone; aliphatic hydrocarbons selected from cyclohexane and hexane; aromatic hydrocarbons selected from toluene and xylene; dimethyl sulphoxide; ethers selected from THF and dioxane; and mixtures thereof. In particular, water and methanol can be used.

In general, the compound of Formula (IV) in the step (d) is treated with thionyl chloride in presence of one or more solvents selected from methylene dichloride, ethylene dichloride, chloroform, chlorobenzene, N,N'-dimethylformamide and dimethyl sulfoxide. Preferably, methylene dichloride.

The chloro intermediate thus formed is treated with metal azide selected from sodium azide or potassium azide. Preferably sodium azide solution in water is used to obtain the compound of Formula (III).

In general, the reaction can be carried out in presence of polar aprotic solvent, which may be selected from dimethyl formamide, dimethyl sulfoxide, acetone, N-methyl pyrrolidine and acetonitrile.

In general, the compound of Formula (III) at step (e) can be reduced by a reducing agent selected from palladium/ammonium acetate, zinc/formic acid, zinc/acetic acid or by hydrogenation under 3-4 kg/cm² hydrogen pressure in the presence of catalyst and one or more solvents to obtain a compound of Formula (II).

In general, the catalyst may be selected from Raney nickel, palladium/carbon, platinum, platinum dioxide. Particularly, Raney Nickel or Pd/C are used.

In Solvent for the reaction can be selected from water, $C_1$-$C_6$-alcohols for example methanol, ethanol, isopropanol, n-butanol, or mixture thereof. In particular, methanol can be used.

In general, the compound of Formula (II) in step (f) is reacted with ethyl(p-tolyl sulfonyl)carbamate or p-toluenesulfonyl isocyanate to obtain grapiprant.

The reaction can be carried out in the presence of base in one or more solvents. In general, the base for the reaction can be selected from sodium hydroxide, potassium hydroxide, lithium hydroxide, sodium carbonate, potassium carbonate lithium carbonate, sodium bicarbonate, potassium bicarbonate, sodium hydride, potassium tert-butoxide or triethyl amine, diisopropyl amine, diisopropylethylamine, pyridine, morpholine, piperidine, DBU, or DABCO. Particularly, triethyl amine can be used.

In general, the solvent for the reaction may be selected from one or more of $C_1$-$C_6$-alcohols selected from methanol, ethanol, isopropanol, 1-butanol and tert-butanol, nitriles selected from acetonitrile and propionitrile, halogenated solvents selected from methylene dichloride, ethylene dichloride, chloroform and chlorobenzene, carbon tetrachloride, aliphatic hydrocarbons selected from cyclohexane and hexane; aromatic hydrocarbons selected from benzene, toluene and xylene, dimethyl sulphoxide; ethers selected from THF and dioxane, esters selected from ethyl acetate, isopropyl acetate, butyl acetate. In particular, toluene or methylene dichloride may be used.

The temperature range for the reaction may be selected from 50 to 100° C. In particular, the reaction is carried out at 80-85° C.

In another general aspect, there is provided a process for preparation of grapiprant as depicted in Scheme-I.

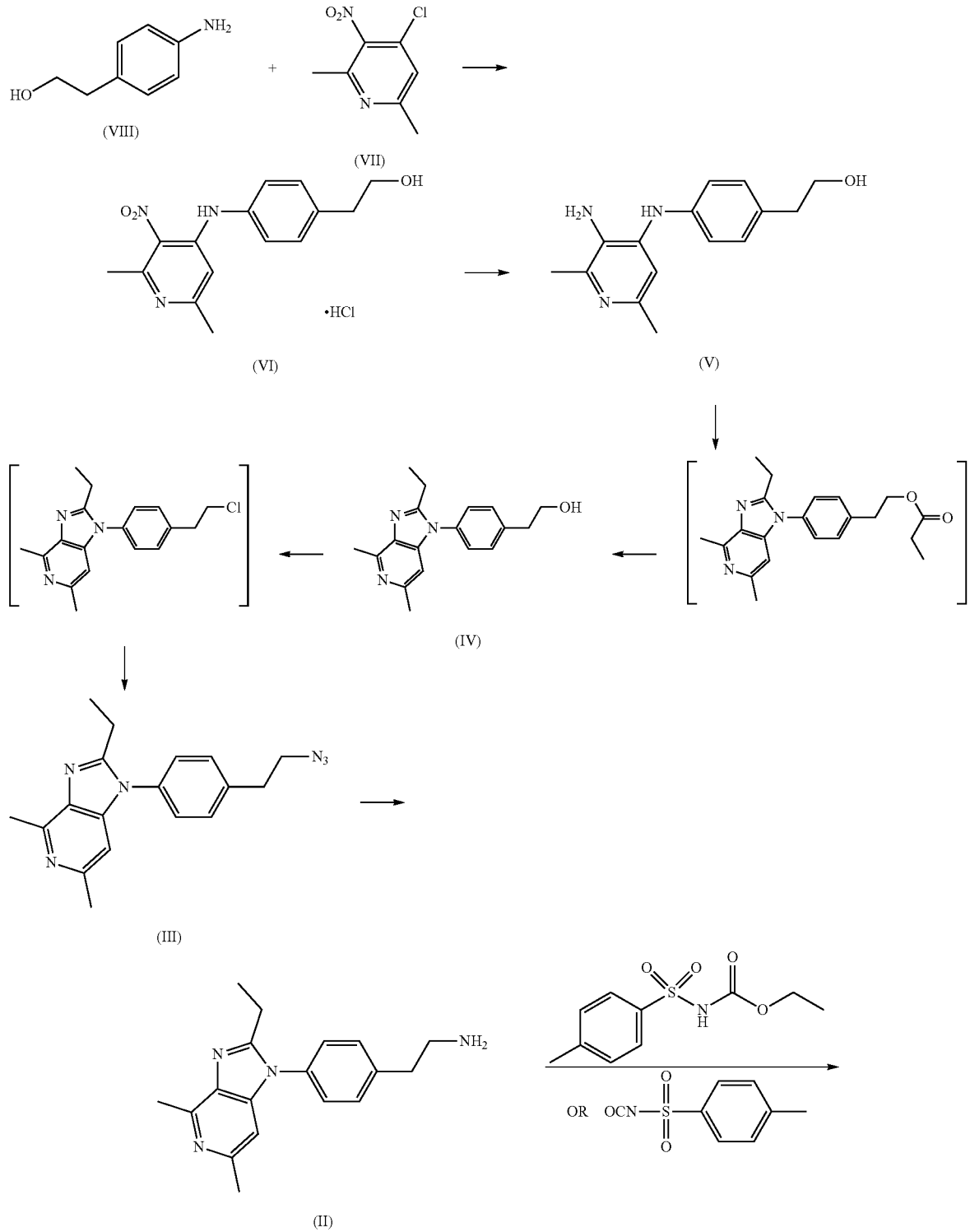

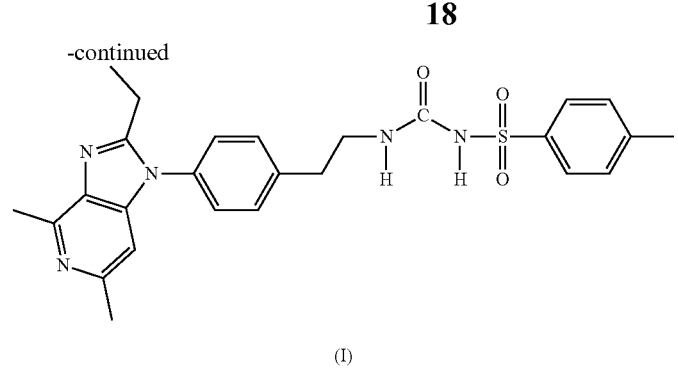

(I)

In another general aspect, there is provided a pharmaceutical composition comprising grapiprant and one or more of compounds of Formula (A), (B), (C), and (D):

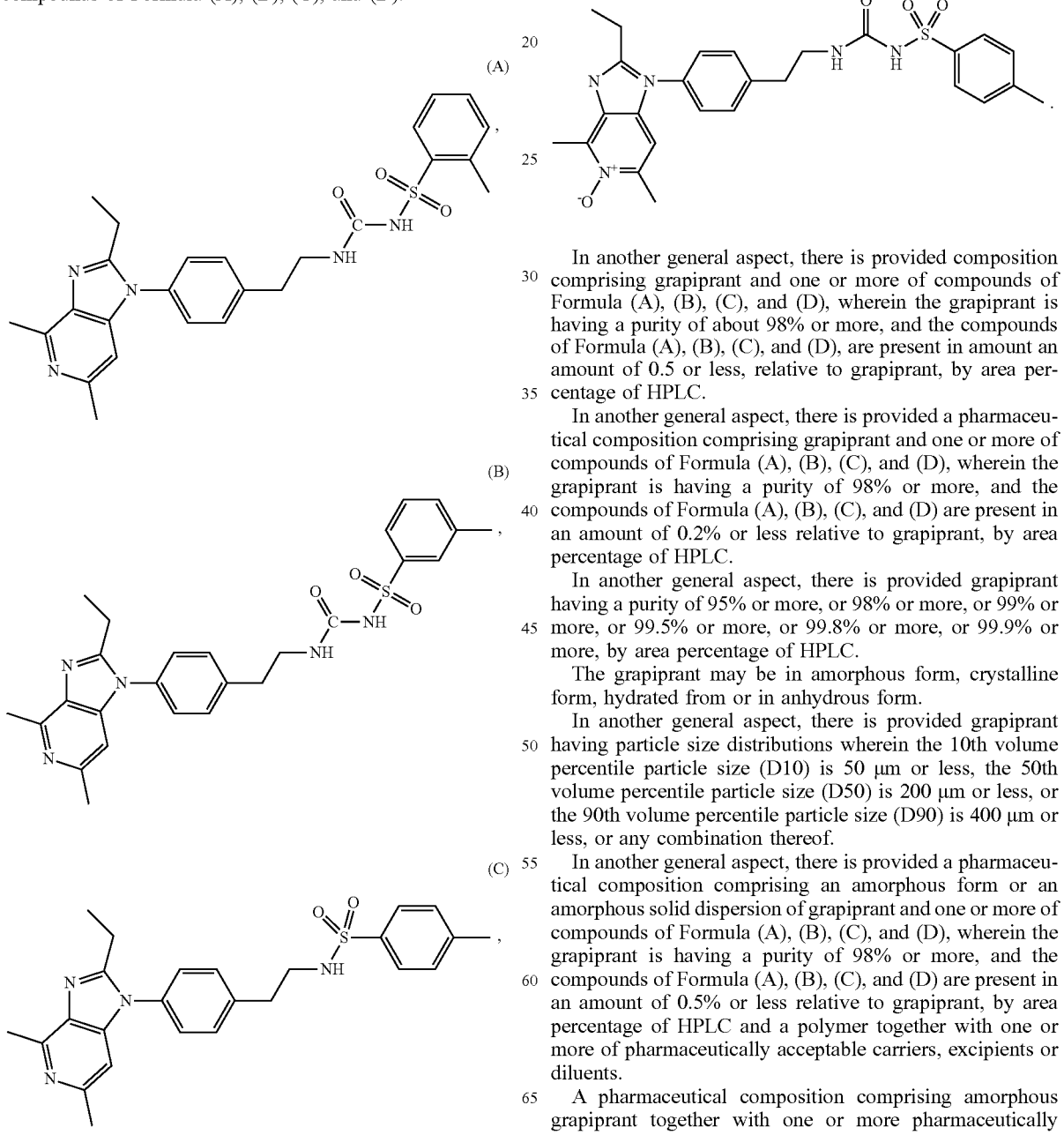

In another general aspect, there is provided composition comprising grapiprant and one or more of compounds of Formula (A), (B), (C), and (D), wherein the grapiprant is having a purity of about 98% or more, and the compounds of Formula (A), (B), (C), and (D), are present in amount an amount of 0.5 or less, relative to grapiprant, by area percentage of HPLC.

In another general aspect, there is provided a pharmaceutical composition comprising grapiprant and one or more of compounds of Formula (A), (B), (C), and (D), wherein the grapiprant is having a purity of 98% or more, and the compounds of Formula (A), (B), (C), and (D) are present in an amount of 0.2% or less relative to grapiprant, by area percentage of HPLC.

In another general aspect, there is provided grapiprant having a purity of 95% or more, or 98% or more, or 99% or more, or 99.5% or more, or 99.8% or more, or 99.9% or more, by area percentage of HPLC.

The grapiprant may be in amorphous form, crystalline form, hydrated from or in anhydrous form.

In another general aspect, there is provided grapiprant having particle size distributions wherein the 10th volume percentile particle size (D10) is 50 μm or less, the 50th volume percentile particle size (D50) is 200 μm or less, or the 90th volume percentile particle size (D90) is 400 μm or less, or any combination thereof.

In another general aspect, there is provided a pharmaceutical composition comprising an amorphous form or an amorphous solid dispersion of grapiprant and one or more of compounds of Formula (A), (B), (C), and (D), wherein the grapiprant is having a purity of 98% or more, and the compounds of Formula (A), (B), (C), and (D) are present in an amount of 0.5% or less relative to grapiprant, by area percentage of HPLC and a polymer together with one or more of pharmaceutically acceptable carriers, excipients or diluents.

A pharmaceutical composition comprising amorphous grapiprant together with one or more pharmaceutically acceptable carriers, excipients or diluents.

A pharmaceutical composition comprising an amorphous solid dispersion of grapiprant and a polymer together with one or more of pharmaceutically acceptable carriers, excipients or diluents.

The examples are set forth to aid in understanding the invention but are not intended to, and should not be construed to limit its scope in any way. The examples do not include detailed descriptions of conventional methods. Such methods are well known to those of ordinary skill in the art and are described in various publications.

EXAMPLES

Example 1: Preparation of Compound of Formula (VI)

In a 500 mL round bottom flask, a solution of compound of Formula (VII) (10 gm, 53.6 mmol) in N-methyl-2-pyrrolidone (17.5 ml) was heated to about 70-75° C. Another solution of compound of Formula (VIII) (7.0 gm 51.03 mmol) was prepared in N-methyl-2-pyrrolidone (10 ml) and added to the above reaction mass. Reaction was maintained at 80-100° C. for 2 hours. After completion of the reaction, it was cooled to the ambient temperature and ethyl acetate was added into the reaction mass. The reaction mass was stirred for an hour at ambient temperature and filtered and washed with ethyl acetate. The product was dried to obtain 2-(4-((2,6-dimethyl-3-nitropyridin-4-yl)amino)phenyl) ethan-1-ol hydrochloride i.e compound of Formula (VI) (15.5 gm, yield 94%).

Example 2: Preparation of Compound of Formula (V)

In 500 mL round bottom flask, a solution of compound of Formula (VI) (30 gm) in methanol (150 ml) was added. Raney Nickel (6 gm, 50% wet) was added and the reaction mass was heated to about 60-70° C. and hydrazine hydrate (80%, 29.1 gm) was added to the reaction mass dropwise. The reaction mass was then maintained at 60-70° C. for 2-4 hours. After completion of the reaction, the reaction mass was cooled to ambient temperature and catalyst was filtered on celite pad and washed with methanol. The solvent was then distilled off under vacuum to obtain a residue. The residue was then dissolved in methanol and then heated to about 50-55° C. and then ethyl acetate was added. The reaction mass was then cooled to 20-30° C. and stirred for one hour. The solids were then filtered and dried to obtain compound of Formula (V) (23.4 gm, yield 98.7%).

Example 3: Preparation of Compound of Formula (IV)

In 500 mL round bottom flask, a mixture of propionic acid (42 ml) and propionic anhydride was added. Compound of Formula (V) (21 gm, 81.6 mmol) was then added to the above reaction mass and heated to about 110-120° C. The reaction mass was stirred for about 6-8 hours and then after completion of the reaction, the reaction mass was cooled to 25-35° C. 25% aqueous sodium hydroxide solution (185 gm) was added and then heated to 60-70° C. and maintained for 8 hours. After completion of reaction the reaction was cooled to ambient temperature and filtered and washed with water and dried to obtain compound of Formula (IV). (16.9 gm, yield 70%).

Example 4: Preparation of Compound of Formula (III)

In a 500 mL round bottom flask, a solution of compound of Formula (V) (15 gm, 50.78 mmol) in dichloromethane (100 mL) was added and the reaction mass was cooled to 0-10° C. A solution of thionyl chloride (7.25 gm, 60.9 mmol) in dichloromethane was then added to the reaction mass at 0-10° C. The reaction mass was then maintained at 10-15° C. for 6 hours. After the completion of the reaction water was added to the reaction mass and (15 ml) and pH of the reaction mass was adjusted to 7-8 by using aqueous sodium carbonate solution. Layer were separated and the organic layer was then concentrated under reduced pressure to obtain 1-(4-(2-chloroethyl)phenyl)-2-ethyl-4,6-dimethyl-1H-imidazo[4,5-c]pyridine (15.4 gm, yield 96.6%).

The above residue was then dissolved in dimethyl formamide (30 mL). Potassium iodide (5.3 gm, 31.86 mmol) and sodium azide (3.1 gm, 47.8 mmol) were then added to the reaction mass and heated to 95-100° C. for 12 hours After completion of the reaction the reaction mass was cooled to ambient temperature. Water was added to the reaction mass to precipitate the product and stirred for 1 hour at ambient temperature. The product was then filtered and dried to obtain 1-(4-(2-azidoethyl)phenyl)-2-ethyl-4,6-dimethyl-1H-imidazo[4,5-c]pyridine i.e. compound of Formula (III) (8.9 gm, yield 87%).

Example 5: Preparation of Compound of Formula (II)

In a 500 mL round bottom flask, a solution of compound of Formula (III) (1.77 gm, 5.52 mmol) in methanol (17.7 ml) and Raney Nickel (0.35 gm, 50% wet) were added. Reaction was then heated to about 65° C. and hydrazine hydrate (80%, 1.72 gm, 27.62 mmol) was added dropwise to the reaction mixture. The reaction mass was then maintained at 65-70° C. for 2 hours. After completion of the reaction the reaction mass was cooled to ambient temperature and catalyst was filtered. Solvent was distilled under vacuum to get the compound of Formula (II) (1.6 gm, yield 98.8%).

Example 6: Preparation of Compound of Formula (I)

In a 500 mL round bottom flask, a solution of compound of Formula (II) (4.5 g, 1.19 mmol) in dichloromethane (10 ml) was added. To the reaction mixture was then added 4-methylbenzenesulfonyl isocyanate (3 g, 1.31 mmol) at 25-35° C. The reaction mass was stirred for 4 hours. After completion of the reaction, solvent was evaporated to obtain a residue. Cyclohexane (45 ml) was added into the residue mass and heated to 65° C. to remove residual dichloromethane. The reaction mass was cooled to 25-35° C. and stirred for an hour. The product was filtered and washed with cyclohexane (13.5 ml). The product was dried at 55° C. for 6 hours to obtain the grapiprant of Formula (I) (7 gm).

Example 7: Preparation of Amorphous Form of Compound of Formula (I)

In 500 mL three necked round bottom flask, 20 g of grapiprant was dissolved in 200 mL of methanol at 25° C. to 50° C. The content was stirred for 30 minutes at 25° C. to 35° C. The solution was filtered through celite bed to get a clear solution of grapiprant. The clear solution was then spray dried by maintaining the inlet temperature in the range of 70° C. under nitrogen pressure of 5 kg/cm$^2$ and maintaining the outlet temperature in the range of 50° C. The product was collected from cyclone and was further dried at 40° C.±5° C. under vacuum for 12 hours to get 17 g of amorphous grapiprant of Formula (I).

Example 8: Preparation of Amorphous Solid Dispersion of Compound of Formula (I)

In 500 mL three necked round bottom flask, 10 g of grapiprant and 100 mL methanol were added. The reaction was stirred for 30 minutes at 25-50° C. to get a clear solution. To the reaction mixture was then added 10 g of co-povidone and allowed to stir at 25-50° C. for 1 hour to get clear solution. The reaction mixture was then filtered through celite to get clear solution. The filtrate was then concentrated. The product was then dried at 50 to 60° C. to obtain 15.0 g amorphous solid dispersion of compound of Formula (I).

Example-9: Preparation of Grapiprant

Step-1:

In a round bottom flask, 40 mL N-methy-2-pyrrolidone and 20 g of 2-(4-aminophenyl) ethyl alcohol were added and the reaction mixture was heated to 40-50° C. for 10-15 minutes to get a clear solution. In an another flask, 40 mL N-methyl-2-pyrrolidone and 28.57 g of 4-chloro-2,6-dimethyl-3-nitropyridine were added and the reaction mixture was stirred at 75-80° C. and the above solution of 2-(4-aminophenyl)ethyl alcohol was added into that within 30-60 minutes at 75-100° C. The reaction mixture was stirred at 80-100° C. for 2 hours. After completion of the reaction, the reaction mixture was cooled to 35-45° C. and 200 mL ethyl acetate was added within 20-40 minutes and stirred at 25-35° C. for an hour. The solid was filtered and washed with ethyl acetate and then dried at 65-70° C. under vacuum for 4 hours to obtain compound of Formula (VI). Yield: 95.34%, Purity: 99.85% w/w by HPLC.

Step-2:

In a round bottom flask, 130 mL water and 40 g of compound of Formula (VI) were added and 50 mL water and 200 mL dichloromethane were added and stirred for 10-15 minutes. 5.2 g sodium hydroxide solution in 20 ml water was added into the reaction mixture at 25-35° C. and stirred for 15 minutes to adjust pH more than 10. The layers were separated and the organic layer was taken into another flask, washed with water and the solvent was distilled. 120 mL methanol and then a slurry of Raney Ni catalyst (8 g Raney Ni in 40 mL methanol) were added into the reaction mixture. The reaction mixture was heated to 63-68° C. 16.4 g of 80% hydrazine hydrate was added within 45-60 minutes and stirred for 2 hours at 63-68° C. After completion of the reaction, the reaction mixture was cooled and filtered. The filtrate was taken in another flask and methanol was distilled out and 240 mL water was added into the reaction mixture and stirred at 25-35° C. for 45-60 minutes and then the solid was filtered and washed with water and then dried at 50-55° C. under vacuum for 8 hours to obtain the compound of Formula (V). Yield: 94.39%, Purity: 97.17% w/w by HPLC.

Step-3:

In a round bottom flask, 50 mL propionic acid and 25 g of compound of Formula (V) and 50 mL propionic anhydride were added and the reaction mixture was stirred at 110-120° C. for 6 hours. The reaction mixture was cooled to 25-35° C. and 50 mL water was added. 40% aqueous NaOH solution was added into the reaction mixture at 25-35° C. to adjust pH above 7 and then 125 mL ethyl acetate was added stirred for 30 minutes. The layers were separated and the organic layer was taken in another flask and the solvent was removed by distillation under vacuum and 50 mL methanol and 50 mL water were added 5.85 g NaOH was added into the reaction mixture and stirred till the completion of the reaction. 150 mL water was added stirred for 30-60 minutes at 25-35° C. The solid was filtered and washed with water and then dried at 70° C. for 6 hours to obtain the compound of Formula (IV). Yield: 76.02%, Purity: 98.95% w/w by HPLC.

Step-4:

In a flask, 160 ml MDC, 20 g compound of Formula (IV) were taken and the reaction mixture was cooled to 15° C. a thionyl chloride solution (9.7 g thionyl chloride in 30 mL MDC) was added the reaction mixture was stirred at 25-35° C. for 3 hours. After completion of the reaction, it was cooled to 20-25° C. and 20 mL water was added and then 15% aq. sodium carbonate solution was added into the reaction mixture to adjust the pH between 6-8. The reaction mixture was stirred for 15 minutes and the layers were separated. The organic layer was taken in another flask and solvent was distilled. 100 mL DMF was added and the reaction mixture was heated to 50-70° C. and 6.6 g sodium azide solution in 40 mL water was added into the reaction mixture. The reaction mixture was stirred to 95-105° C. for 6 hours. After completion of the reaction, it was cooled to 25-35° C. and 280 mL water was added and stirred at 25-35° C. for around 2 hours. The solid was filtered and washed with water and then dried at 65° C. under vacuum for 6 hours to obtain the compound of Formula (III). Yield: 82.98%, Purity: 98.76% w/w by HPLC.

Step-5:

In an autoclave, 75 mL methanol, 15 g compound of Formula (III) and 3 g Raney nickel with 30 mL methanol were added under nitrogen atmosphere. The reaction mixture was stirred under 3-4 kg/cm2 hydrogen pressure at 40-45° C. After completion of the reaction, the reaction mass was cooled to 25-35° C. and filtered and washed with methanol. The filtrate was taken in another flask and the solvent was removed by distillation under vacuum below 60° C. 75 mL water and 75 mL MDC were added into the reaction mixture and pH was adjusted to 5.5 to 6.5 using conc. hydrochloric acid and stirred for 15 minutes. The layers were separated and the aqueous layer was taken in another flask and 75 mL MDC was added. pH was adjusted using 25% aqueous solution of NaOH and the reaction mixture was stirred. The layers were separated and the organic layer was taken in another flask and the solvent was distilled out to obtain a viscous oil. 3 mL MDC and 75 mL cyclohexane were added and the reaction mixture was stirred for 2 hours. The solid was filtered and washed with cyclohexane and then dried at 50-55° C. under vacuum for 6 hours to obtain the compound of Formula (II). Yield: 81.88%, Purity: 98.96% w/w by HPLC.

Step-6:

(a) Preparation of Ethyl (p-tolylsulfonyl)carbamate

In a flask, 300 mL acetone, 25 g p-toluene sulfonamide and 53.5 g powdered K$_2$CO3 with 25 mL acetone were added. The reaction mixture was heated to 55-60° C. and stirred for 30 minutes. A solution of 21.07 g ethyl chloroformate in 50 mL acetone was added into the reaction mixture within 30-45 minutes and stirred at 55-60° C. for 2 hours. After completion of the reaction, the reaction mixture was cooled to 25-35° C. and 500 mL water was added and the pH of the reaction mass was adjusted to 3.5-4.5 using conc. HCl. 250 mL MDC was added into the reaction mixture and stirred for 30 minutes. The layers were settled and separated. The organic layer was taken in another flask and solvent was removed by distillation and 75 mL cyclohexane was added and stirred for one hour at 25-35° C. The solid was filtered and washed with cyclohexane and then dried at 50° C. under vacuum or 4 hours to obtain ETC.

(b) Preparation of Grapiprant

In a 500 mL, 4 neck round bottom flask, 100 mL toluene, 11 g compound of Formula (II), 7.56 g triethyl amine and 11 g ethyl (p-tolylsulfonyl) carbamate with 10 mL toluene were added. The reaction mixture was stirred at 80-90° C. for 4 hours. After completion of the reaction, the reaction mixture was cooled to 25-35° C. and 44 mL water was added and stirred for 15 minutes. The layers were separated and the aqueous layer was taken in another flask and 55 mL ethyl acetate was added and pH was adjusted to 1-3 using conc. hydrochloric acid and stirred for 15 minutes. The layers were separated and the aqueous layer was taken in another flask and 55 mL ethyl acetate was added and stirred for 2-3 hours. The solid was filtered and washed with 11 mL water and 22 mL ethyl acetate. The solid was taken into another flask and 55 mL water and 55 mL MDC were added. A solution of 4 g sodium bicarbonate in 46 mL water was added into the reaction mixture at 25-35° C. to adjust pH to 7-7.5 and stirred for 15-30 minutes at 25-35° C. The layers were separated and the aqueous layer was washed with 22 mL MDC. The organic layer was taken into another flask and the solvent was distilled out under vacuum and 77 mL cyclohexane was added. The reaction mixture was cooled to 25-35° C. and stirred for 30 minutes. The solid was filtered and washed with 22 mL cyclohexane and dried at 65-70° C. under vacuum for 6 hours to obtain grapiprant.

Example-10: Preparation of Grapiprant

In a 2 L, 4 neck round bottom flask, 720 mL toluene, 80 g compound of Formula (II), 55 g triethyl amine and 80 g ethyl (p-tolylsulfonyl)carbamate with 80 mL toluene were added and stirred at 80-90° C. for 4 hours. After completion of the reaction, the reaction mixture was cooled to 25-35° C. and 320 mL water was added and stirred for 15 minutes. The layers were separated and the aqueous layer was taken in another flask and 400 mL ethyl acetate was added and pH was adjusted to 1-3 using conc. hydrochloric acid and stirred for 15-30 minutes. The layers were separated and the aqueous layer was taken in another flask and 400 mL ethyl acetate was added and stirred for 2-3 hours. The solid was filtered and washed with 80 mL water and 160 mL ethyl acetate. The solid was taken into another flask and 400 mL water and 400 mL MDC were added. A solution of 30 g sodium bicarbonate in 345 mL water was added into the reaction mixture at 25-35° C. to adjust pH to 7-8 and stirred for 15-30 minutes at 25-35° C. The layers were separated and the aqueous layer was washed with 22 mL MDC. The organic layer was taken into another flask and the solvent was distilled out under vacuum. After distillation, 640 mL acetone was added and the mixture was heated to 50-60° C. and acetone was distilled between 240 mL to 320 mL. The reaction mixture was stirred at 50-60° C. for 3-4 hours then cooled to 25-35° C. and stirred at this temperature for 90-120 minutes. The solid was filtered and washed with acetone and then dried to obtain grapiprant.

Example-11: Preparation of Amorphous Grapiprant

In a Round bottom flask, 630 mL methanol and 70 g grapiprant were added and stirred at 25-35° C. to get a clear solution. This solution was fed into spray dryer using peristaltic pump at 10-12% pump speed and spray dried to obtain amorphous grapiprant.

Spray Drying Parameters:

| Buchi Spray Dryer Model | B-290 Mini spray dryer with Inert loop B-295 and Dehumidifier B-296 |
|---|---|
| Inlet temperature set (° C.) | 70-75 |
| N2 pressure (Kg/cm$^2$) | 3-4 |
| Aspirator-Mower RPM | 65-85% |
| Peristaltic pump RPM | 10-12% |

Example 12: Preparation of Compound of Formula (D)

In a round bottom flask, 1 g N-((4-(2-ethyl-4,6-dimethyl-1H-imidazo[4,5-c]pyridin-1-yl)phenethyl)carbamoyl)-4-methylbenzene sulfonamide was stirred with 10 mL chloroform at 25-35° C. 0.431 gm m-chloroperbenzoic acid was added and stirred at ambient temperature for 24 hours. After completion of the reaction, 10 mL water was added into that and stirred for 15-20 minutes and layers were separated. Organic layer concentrated under vacuum to get residue. Purification of the product was performed using silica gel (60-120 mesh) column chromatography and product eluted using 10% methanol/MDC followed by concentration to obtain the compound of Formula (D) i.e. N-oxide Grapiprant.

While the present invention has been described in terms of its specific embodiments, certain modification and equivalents will be apartment to those skilled in the art and are intended to be included within the scope of the present invention.

We claim:

1. A composition comprising grapiprant having a purity of about 98% or more, and one or more compounds of Formula (A), (B), (C), and (D), in an amount of about 0.5% or less, relative to grapiprant, by area percentage of HPLC:

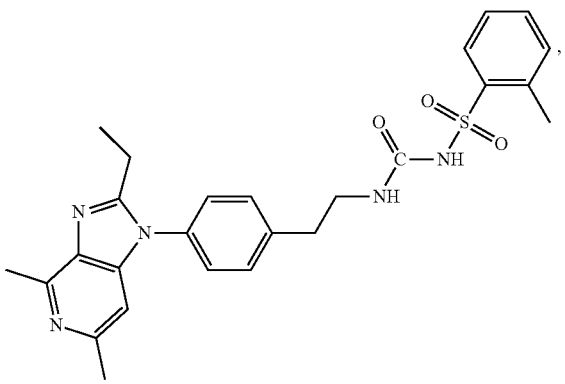

(A)

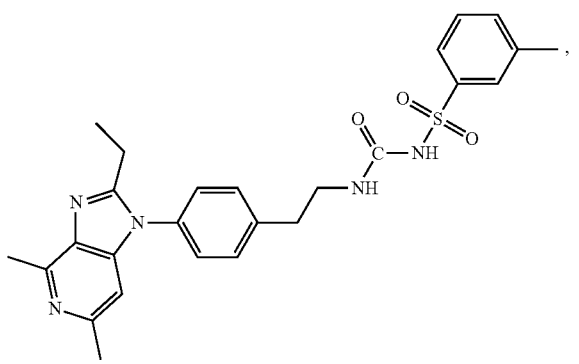

(B)

(C)

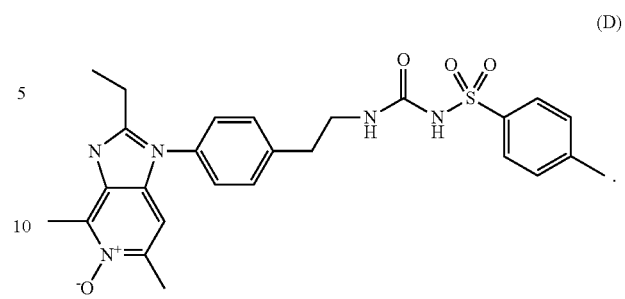

(D)

2. The composition according to claim 1, wherein the grapiprant is in an amorphous form.

3. The composition according to claim 1, wherein the composition further comprising one or more pharmaceutically acceptable carriers, excipients, and diluents.

4. The composition according to claim 1, wherein the grapiprant is having particle size distributions, wherein the 10th volume percentile particle size (D10) is 50 μm or less, the 50th volume percentile particle size (D50) is 200 μm or less, or the 90th volume percentile particle size (D90) is 400 μm or less, or any combination thereof.

* * * * *